US00RE37153E

(19) United States
(12) Reissued Patent
Henszey et al.

(10) Patent Number: US RE37,153 E
(45) Date of Reissued Patent: May 1, 2001

(54) VARIABLE PRESSURE REDUCING DEVICE

(75) Inventors: Richard R. Henszey, Oconomowoc; Bruce W. Weiss, Whitefish Bay, both of WI (US)

(73) Assignee: Sentry Equipment Corp., Oconomowoc, WI (US)

(21) Appl. No.: 08/518,266

(22) Filed: Aug. 23, 1995

Related U.S. Patent Documents

Reissue of:
(64) Patent No.: 5,333,648
Issued: Aug. 2, 1994
Appl. No.: 07/959,068
Filed: Oct. 13, 1992

(51) Int. Cl.[7] ..... F15D 1/02
(52) U.S. Cl. ..... 138/26; 138/46; 277/205
(58) Field of Search ..... 138/26, 30, 43–46; 137/14; 251/214, 264, 266; 277/205, 188 A; 73/863.81, 863.86

(56) References Cited

U.S. PATENT DOCUMENTS 1,152,127 * 8/1915 Stackpole ..... 138/45
2,091,613 * 8/1937 Polston ..... 73/863.01
2,240,119 * 4/1941 Montgomery et al. ..... 138/45 X
3,062,055 * 11/1962 Bills ..... 73/863.02
3,203,250 * 8/1965 Coggeshall et al. ..... 73/863.1
3,469,591 * 9/1969 Odendahl ..... 137/14
3,598,149 * 8/1971 Witkin ..... 137/599
3,730,203 * 5/1973 Katzer et al. ..... 137/14
4,106,525 * 8/1978 Currie et al. ..... 138/43
4,127,627 * 11/1978 Sarto ..... 138/45 X
4,169,604 * 10/1979 Heathcott ..... 277/205 X
4,196,912 * 4/1980 Quitberg ..... 277/205 X
4,317,379 * 3/1982 Oberlander et al. ..... 73/863.12
4,340,234 * 7/1982 Ise ..... 279/3
4,476,772 * 10/1984 Gorman et al. ..... 277/205 X
4,631,967 * 12/1986 Welker ..... 73/861.25
4,706,970 * 11/1987 Ramirez ..... 277/205
5,005,432 * 4/1991 Faulkner ..... 73/3.41
5,163,692 * 11/1992 Schofield et al. ..... 277/205 X

OTHER PUBLICATIONS

American Veriseal Corp. brochure, Catalog No. AV984, 1984.*
Sentry—"VREL Sample Pressure Reducing Device Application Bulletin", Jan. 1989.*

* cited by examiner

*Primary Examiner*—Patrick Brinson
(74) *Attorney, Agent, or Firm*—Jansson, Shupe, Munger & Stomma, Ltd.

(57) ABSTRACT

A variable pressure reducing device for reducing high pressure in steam and hot water samples forces the liquid through an annular passageway between a pair of rods within a complementary pair of tubes. The flow rate through the rod-in-tube device, or the pressure drop across the device, is adjustable by means of a rotatable guide screw for adjusting the position of the rods within the tubes. The rods are tapered to provide a smooth flow of liquid through the device. The seal around the guide screw is self energized by means of a seal jacket between a valve gland and a stem portion of the guide screw constructed so that the biasing force of a spring on the seal jacket is supplemented by pressure from liquid flowing through the device The guide screw is centered within the valve gland to keep the guide screw properly aligned, particularly when the device is used with a motor for rotating the guide screw to adjust the position of the rods.

21 Claims, 2 Drawing Sheets

VARIABLE PRESSURE REDUCING DEVICE

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a variable pressure reducing device to reduce the pressure and control the flow of high pressure liquids. In particular, the invention relates to a rod-in-tube-type pressure reducing device with an improvement in construction of the rods to smooth the flow of liquid through the device and an improvement in the sealing means to provide easier adjustability of the device.

2. Background of the Art

Numerous applications of high pressure fluid systems require, at some point in the system, reduction of the pressure to allow safe handling of the fluid. For instance, a sample withdrawn from a steam and hot water system in a power plant must be reduced in pressure before the sample can be introduced into analyzing instrumentation or handled safely by plant personnel. A number of devices are used in the power plant industry to reduce the high pressure of steam and hot water, such as fixed orifice valves or pressure regulators, but material erosion frequently experienced in such devices can lead to loss of function. Capillary tubing, also commonly used to reduce high pressure in liquid samples, may become blocked by crud or scale, requiring complete shutdown of the sample line while the capillary tubing is cleaned or replaced.

Another type of device for reducing high pressure in liquids is applicant's earlier version of a variable pressure reducing element (VREL™). The VREL is a rod-in-tube device in which the pressure of an incoming liquid is reduced as the liquid is forced to travel through a narrow gap between a stepped rod and the inner diameter of a tube. Because the work is done over the entire length of the stepped rod, localized stresses are held to a minimum, resulting in a very long service life compared with orifice valves and pressure regulators in which the pressure drop is taken over a very short distance. The flow through the VREL, or the pressure drop across it, can be adjusted while the liquid is flowing through the device by changing the position of the rods in the tubes. Turning the handle in one direction or the other moves the rods in or out of the tubes. If crud blocks the flow of liquid, the rods can be fully retracted to allow the high pressure liquid to blow the dirt through the device.

This earlier version of the VREL, however, has a number of drawbacks and disadvantages. The flow past the steps in the stepped rod causes turbulence and unsteady liquid flow, which is undesirable particularly when the device is used in connection with applicant's new automated sample conditioning panel (which is the subject of a co-pending application). Scale and crud also have a tendency to build up on the steps of the stepped rod, inhibiting flow through the device.

In the earlier version of applicant's VREL device, a packing seal, comprised of a thick Teflon ™ ring sandwiched between two washers and compressed ("packed") within a valve gland by a threaded nut, caused high compressive forces making it difficult to adjust the device. A leak in the seal would typically be fixed by plant personnel merely tightening the nut further, which in turn simply increased the compressive forces and making it further difficult to adjust the device.

SUMMARY OF THE INVENTION

An improved variable pressure reducing device comprising an adjustable rod-in-tube construction, with smoother flow and easier adjustability than earlier devices, is disclosed.

Flow through the device is improved by tapering the rods, thereby eliminating the turbulence caused by the stepped rods experienced in the earlier version of the device. Adjustability of the device is greatly improved by replacing the packing seal with a spring biased seal jacket which is not dependent on compressive forces to seal the device. The seal jacket is also uniquely designed to utilize the high pressure liquid within the device to enhance the sealing characteristics of the seal jacket, thereby providing, in effect, a self-energized seal. The invention is further provided with a means for centering and adjusting an internal guide screw, used to adjust the position of the rods within the tubes, for adapting a device for use in motorized applications.

The primary objects of the invention are therefore to provide a variable pressure reducing device comprising a pair of rods adjustably inserted within a pair of tubes for reducing high pressure liquid samples over the length of the rods; to provide a relatively smoother flow of liquid through the device by gradually tapering the rods as compared with the stepped rod design of applicants earlier device; to provide an improved, self-energized sealing means which allows easy adjustment of the device; to adapt the device for use with motorized adjustment means; and, to provide an improved variable pressure reducing device adapted especially for use on an automated sample conditioning system.

Other objects and advantages of the invention will become apparent from the following description taken in connection with the accompanying drawings which set forth, by way of illustration and example, certain preferred embodiments of the invention.

BRIEF DESCRIPTION OF THE DRAWINGS

The drawings, which are a part of the specification and which present exemplary embodiments of the present invention, include the following.

DETAILED DESCRIPTION OF THE INVENTION

Figure 1:
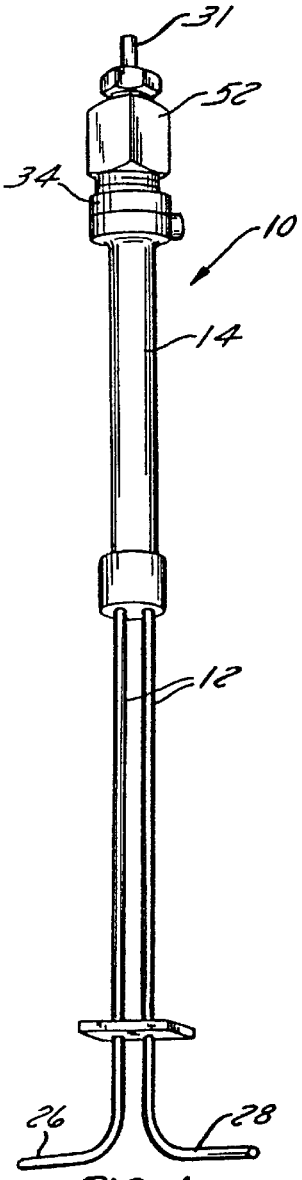
FIG. 1 is a front plan view of an improved variable pressure reducing element (VREL ™) constructed in accordance with the principles of the present invention.
Figure 2:
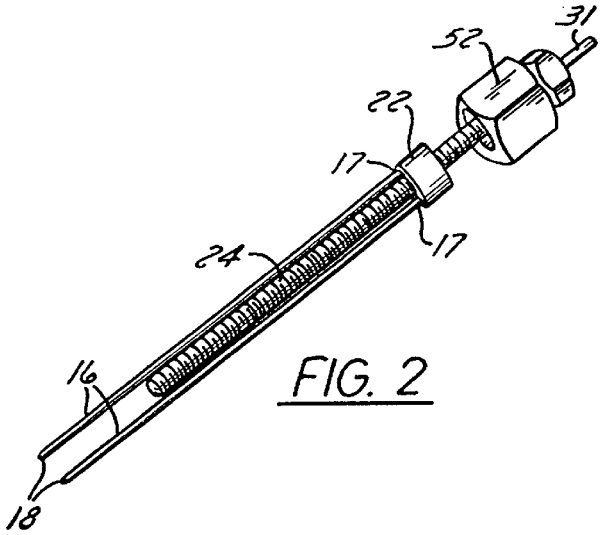
FIG. 2 shows the internal rods which fit within the tubes, and a guide screw for adjusting the position of the rods within the tubes of the variable pressure reducing element.

A variable pressure reducing element (VREL ™) 10 is used to reduce the pressure and control the flow of high pressure liquids. The device 10 is especially useful for reducing the pressure of steam and hot water samples in a power plant front as high as 5000 psi down to about 50 psi so that the liquid can be safely piped to an analyzer instrument or handled manually for a grab sample.

The VREL 10 is a rod-in-tube pressure reducing, flow control device comprising two stainless steel tubes 12 joined to one end of a larger tube or barrel 14. A pair of tapered rods 16 [is] *are* inserted into the two tubes 12. One end 17 of each rod 16 is connected to a threaded ring 22 on a threaded guide screw 24 within the barrel 14. The other end 18 of each rod 16 is rounded. Between the ends 17 and 18, the rod 16 is smoothly tapered from a relatively wide diameter at the end 17 which is connected to the threaded ring 22 down to a relatively narrow diameter at the rounded end 18 of the rod 16. The tubes 12 have a fixed inner diameter throughout their length.

The liquid enters the VREL 10 at inlet 26 and exits from outlet 28. The pressure of the incoming liquid is reduced as the liquid is forced to travel through the progressively narrower annular gap 30 between the outer diameter of the tapered rod 16 and the inner diameter of tube 12. Taking the change in pressure over a long length eliminates the problem of hydrogen ion dissociation. The pressure drop through the VREL 10 is a function of the length of the rods 16 which are inserted into the tubes 12, i.e. the pressure drop across the VREL 10 is adjustable by changing the location of the rods 16 within the tubes 12.

The flow through the VREL 10 can be adjusted, even while the liquid is flowing through it, by changing the position of the rods 16 in the tubes 12. By rotating the threaded guide screw 24 in one direction or the other, the threaded ring 22 moves the tapered rods 16 in or out of the tubes 12. The position of the rods 16 within the tubes 12, together with the tapered characteristic of the rods 16, control the pressure drop and flow rate of the liquid through the VREL 10. In the event of a crud burst becoming lodged in the space between the rod 16 and tube 12, the VREL 10 can be cleared by backing off the rods 16 until the obstruction is blown free. Furthermore, the tapering of the rods 16 provides a smooth liquid flow through the device which is desirable for application of the VREL on an automated sample conditioning system. The smooth taper of the rods causes no flow disturbances which may lead to unsteady flow rate (the stepped rods caused unsteadiness at certain positions).

As the liquid flows through the VREL 10, the liquid exerts a frictional force against the inlet rod in a direction toward the top end of the VREL 10 (i.e. toward the threaded ring 22), and a downward force against the outlet rod. Under optimal operating conditions, the forces approximately balance each other. The balanced arrangement facilitates low mechanical stress on the valve for easy adjustment and promotes long valve life. As crud builds up on the rods, however, a large unbalanced force may develop tending to push the rods 16 and the guide screw 24 up and out of the VREL device 10. For this reason, the VREL sealing means is designed to hold down a large upward directed force in the device.

Figure 3:
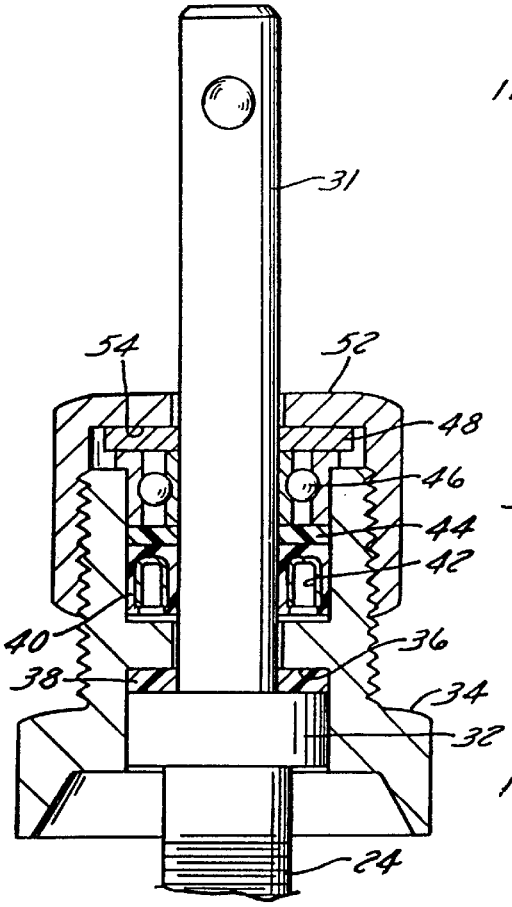
FIG. 3 is a cross sectional view of the seal assembly of the variable pressure reducing element.
Figure 4:
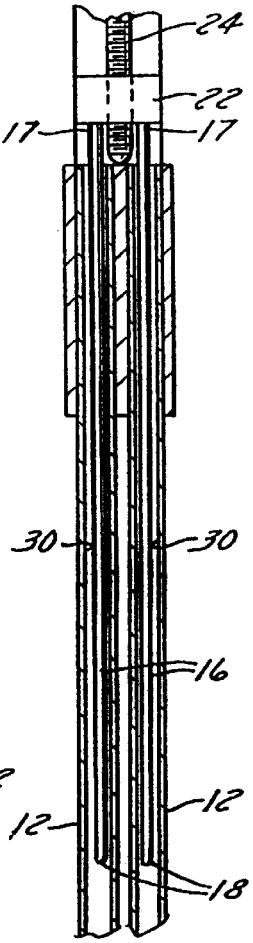
FIG. 4 is a cross-sectional view showing the rods within tubes.
Figure 6:
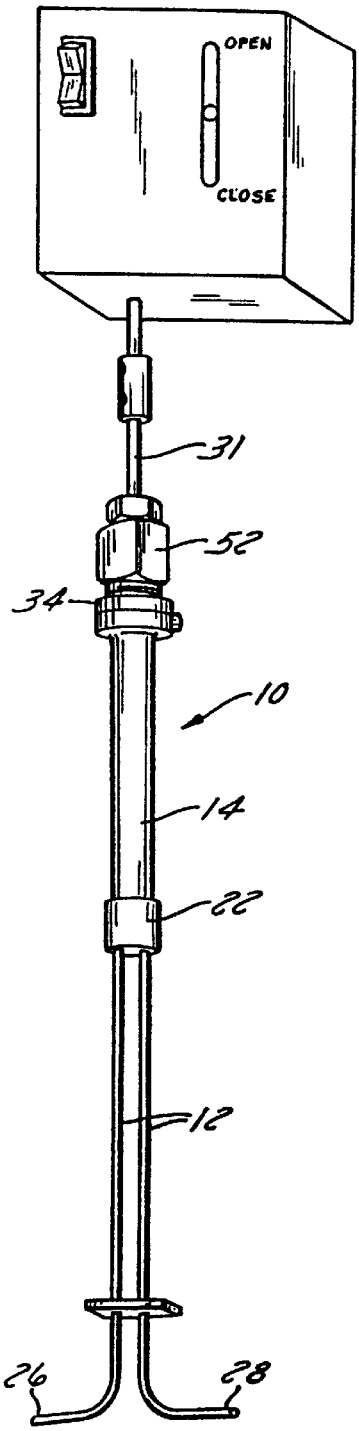
FIG. 6 is a front plan view showing a direct drive motor for adjusting the rods.
Figure 7:
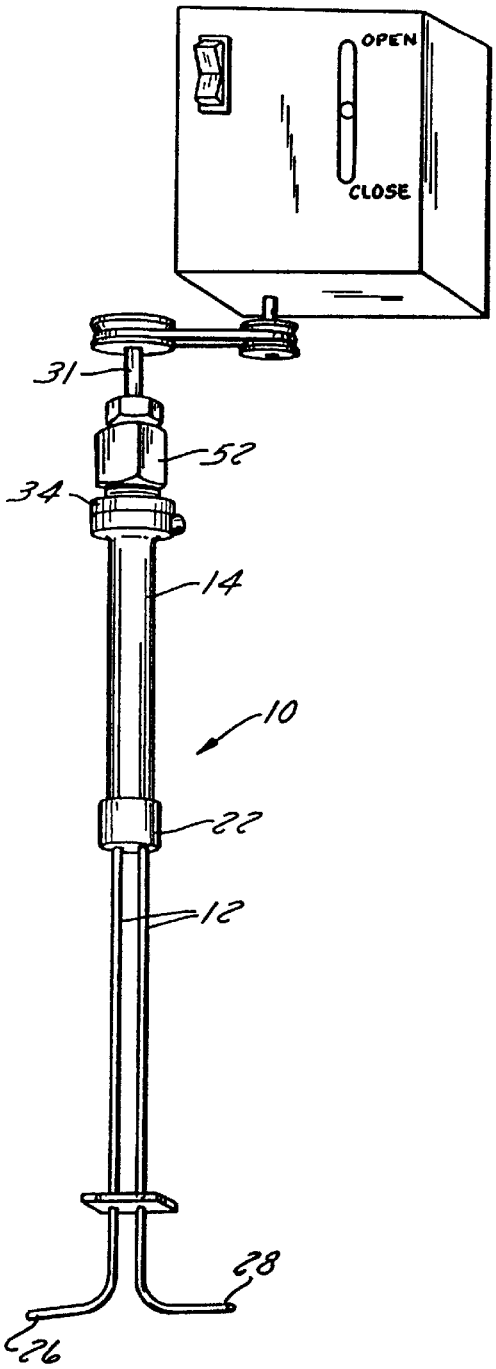
FIG. 7 is a front plan view showing a belt drive motor for adjusting the rods.

The VREL sealing means, shown in FIG. 3, comprises a valve gland 34 placed on the top end of the barrel 14, i.e. opposite the tapered rods 16. The valve gland 34 has an internal annular ridge seat 36 with a central opening. An upper stem portion 31 of the guide screw 24 projects through the central opening of the annular ridge 36 on the gland 34. An annular shoulder 32 on the guide screw 24 complementary to the ridge seat 36 of the gland 34 holds the guide screw 24 within the barrel 14. A thrust washer 38 is placed between the shoulder 32 on the guide screw 24 and the ridge seat 36 of the gland 34. The thrust washer 38, despite being compressed between the shoulder 32 of the guide screw 24 and the ridge seat 36 of the gland 34, permits the guide screw 24 to turn fairly easily relative to the gland. The thrust washer 38 should be made of a low friction material which causes negligible contamination to the liquid flowing through the device, such as PEEK ™ Teflon ™, nylon, acetal or other suitable material. PEEK ™ is a high lubricity material (i.e. very smooth, low friction material)available from LNP Engineering Plastics, Malvern, Pa.

The seal is designed to facilitate easy rotation of the guide screw 24 with relatively low torques, and to be effectively self-energizing by utilizing the pressure from the liquid flowing through the device. A Teflon ™ jacket 40 with a U-shaped cross section is placed in an annular space formed by the inner diameter of the wall of the gland 34 and the outer diameter of the stem portion 31 of the guide screw 24. Inner and outer wall portions of the Teflon jacket 40 provide a seal against the outer diameter of the guide screw 24 and the inner diameter of the gland 32, respectively. An annular spring 42 placed within the channel of the U-shaped jacket 40 presses the inner wall portion of the jacket 40 against the outer diameter of the guide screw 24, and presses the outer wall portion of the jacket 40 against the inner diameter of the wall of the gland 34. Further, pressurized liquid "leaking" up through narrow gaps past the guide screw shoulder 32, thrust washer 38 and ridge seat 36 provides additional force to press the walls of the jacket 40 against the outer diameter of the guide screw 24 and the inner diameter of the gland 34. The sealing effect of the jacket 40 is therefore effectively self-energized in that high pressure liquid within the VREL 10 acts in cooperation with the seal jacket 40 and spring 42 to improve the seal.

On the "dry" side, a backup washer 44 also made of PEEK ™ is placed against the upper side of the Teflon jacket 40. Teflon under high pressure has a tendency to flow, so the PEEK ™ backup washer 44 inhibits distortion of the Teflon jacket 40 to maintain its integrity and sealing capability. The PEEK ™ backup washer 44 is very hard and has no gaps, and it also has a close fit around the outer diameter of the guide screw 24 and inner diameter of the gland 34.

In applications in which a motor is used to turn the guide screw 24 to adjust the rods 16 within the tubes 12, it is important to ensure that the guide screw 24 remains centered in the device. Two types of motor drive units have been designed and tested for use with the VREL device disclosed herein—a direct drive and a belt drive. In a belt drive, the drive axis of the motor is displaced laterally from the axis of the guide screw 24, and the drive axis of the motor is connected to the stem portion 31 of the guide screw 24 with a V-belt assembly. Since the V-belt assembly places a lateral load on the guide screw, a bearing 46 is used to center the guide screw 24 in the gland 34. The lower portion of the bearing 46 fits within the annular space inside the gland 34 with the bottom face of bearing 46 abutting the top surface of the backup washer 44. The bearing 24 has an annular flange which fits on the upper surface of the gland 34. The bearing 46, made of stainless steel, keeps the guide screw 24 centered and provides for relatively easy rotation of the guide screw even with a lateral load applied against it by the belt drive motor. A bearing washer 48 placed over the bearing 46 provides support over the entire top surface area of the bearing 46.

Figure 5:
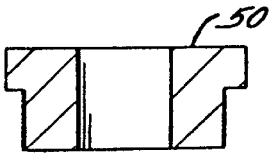
FIG. 5 is a cross-sectional view of a bushing which, in some applications, can be used in place of the bearing and washer shown in FIG. 3.

In applications where very little lateral loading of the guide screw [46] *24* is expected, like in the case of a direct drive motor where the drive axis of the motor aligned with the axis of the guide screw 24, a bronze bushing 50 as shown in FIG. 5 may be used in place of the bearing 46 and washer 48. A threaded nut 52 with a central opening is placed over the stem portion 31 of the guide screw 24 and threaded onto the top of the valve gland 34. Thus, the shoulder 32 of the guide screw 24 holds the guide screw 24 within the gland 34, and the nut 52 then holds the seal jacket 40 and spring 42, backup washer 44, bearing 46 and bearing washer 48 (or bushing 50) within the gland 34.

We claim as our invention:

1. A variable pressure reducing device comprising:

a barrel;

a pair of tubes joined to one end of the barrel;

a pair of rods adjustably insertable within the tubes with each rod having a relatively wide diameter at an upper end of the rod, a relatively narrow diameter at a lower end of the rod, and a smooth tapered outer surface extending from the upper end to the lower end;

a rotatable guide screw and complementary threaded ring within the barrel for adjusting the rods;

a valve gland, including an internal annular ridge seat with a central opening therein, placed over the other end of the barrel;

the threaded guide screw having an annular shoulder complementary to the ridge seat and having a stem portion projecting through the central opening of the gland;

a low friction thrust washer between the shoulder of the guide screw and the ridge seat of the gland;

an annular seal jacket between the stem portion of the guide screw and an inner wall of the gland;

a spring for biasing an inner wall portion of the jacket against the stem portion of the guide screw and for biasing an outer wall portion of the jacket against the inner wall of the gland;

a back-up washer abutting against the seal jacket;

annular centering means for centering the stem portion of the guide screw within the gland; and a nut with a central opening placed over the stem portion of the guide screw and threaded over the gland.

2. The variable pressure reducing device according to claim 1, wherein the centering means comprises a bearing and washer.

3. The variable pressure reducing device according to claim 1, wherein the centering means comprises a bushing.

4. The variable pressure reducing device according to claim 1 further comprising a motor for rotating the guide screw to adjust the position of the rods within the tubes.

5. The variable pressure reducing device according to claim 1, wherein pressure from liquid flowing through the device further presses the seal jacket against the guide screw and gland wall.

6. A variable pressure reducing device for reducing high pressure of liquids comprising:

a pair of rods adjustably insertable within a complementary pair of tubes by means of a rotatable guide screw;

each rod having a smooth outer surface tapered from a relatively wide diameter at an upper end of the rod down to a relatively narrow diameter at a rounded lower end of the rod;

the guide screw being held within a barrel by a valve gland;

a seal jacket within an annular space formed by the outer diameter of a stem portion of the guide screw and the inner diameter of a wall of the gland;

a spring for biasing an inner wall section of the seal jacket against the stem portion of the guide screw and for biasing an outer wall section of the seal jacket against the gland wall;

a washer abutting the seal jacket; and, centering means for centering the stem portion of the guide screw within the gland.

7. The variable pressure reducing device according to claim 6, wherein the guide screw is held within the barrel by the valve gland by means of an annular ridge seat within the gland, a complementary annular shoulder on the guide screw, and a thrust washer between the shoulder and ridge seat.

8. The variable pressure reducing device according to claim 8, wherein the centering means comprises a bearing and washer.

9. The variable pressure reducing device according to claim 8, further comprising a belt drive motor for rotating the guide screw to adjust the position of the rods within the tubes.

10. The variable pressure reducing device according to claim 7, wherein the centering means comprises a bushing.

11. The variable pressure reducing device according to claim 10, further comprising a direct drive motor for rotating the guide screw to adjust the position of the rods within the tubes.

12. An improved variable pressure reducing device of the type which includes a pair of tubes joined to one end of a barrel, a complementary pair of rods adjustably connected to a threaded ring on a rotatable threaded guide screw within the barrel, the pair of rods being insertable within the pair of tubes, respectively, thereby forming a passageway between the outer diameter of the rods and the inner diameter of the tubes for fluid to flow therethrough, the improvement comprising tapering the rods with a smooth outer surface from a relatively wide diameter at an upper end of the rod which is connected to the threaded ring down to a relatively narrow diameter at an opposite rounded end of the rod to form a progressively narrower annular passageway to smooth the flow of fluid therepast.

13. The improved variable pressure reducing device according to claim 12, further comprising an improvement in the sealing means of the device comprising:

a valve gland on the other end of the barrel including an internal annular ridge seat and a central opening therein;

the guide screw having an annular shoulder complementary to the ridge seat and a stem portion projecting through the central opening of the gland;

a low friction thrust washer between the shoulder of the guide screw and the ridge seat of the gland;

a seal jacket in an annular space formed by the inner diameter of a wall of the gland and the outer diameter of the stem portion of the guide screw;

a spring for biasing the seal jacket against the wall of the gland and the stem portion of the guide screw;

a washer abutting the seal jacket;

centering means for centering the guide screw; and, a nut over the open end of the annular space in the gland.

14. The variable pressure reducing device according to claim 13, wherein the centering means comprises a bearing and washer.

15. The variable pressure reducing device according to claim 13, wherein the centering means comprises a bushing.

16. The variable pressure reducing device according to claim 13, wherein pressure from liquid flowing through the device further presses the seal jacket against the guide screw and gland.

17. The variable pressure reducing device according to claim 16, further comprising a motor connected to the stem portion of the guide screw for motorized adjustment of the position of the rods within the tubes.

*18. A variable pressure reducing device for reducing high pressure in steam and liquid sampling lines, said device comprising:*

*at least one tube forming at least one elongate passageway, wherein said at least one elongate passageway has an inlet end for receiving fluid at an elevated first pressure and an exit end for discharging fluid at a second pressure lower than said elevated pressure;*

*at least one elongate rod mounted for movement in said at least one elongate passageway, wherein said at least one elongate rod has a first end and a second end such that said at least one elongate rod is smoothly tapered from said first end to said second end for providing a substantial pressure loss therealong;*

*an adjustment mechanism for moving said at least one elongate rod into and out of said at least one elongate passageway, wherein said adjustment mechanism is connected to said first end of said at least one elongate rod; and*

*an annular gap between said at least one elongate rod and said at least one elongate tube wherein said annular gap becomes progressively narrower along said at least one elongate rod in a linear direction from said first end of said at least one elongate rod to said second end of said at least one elongate rod.*

*19. The device of claim 18 wherein said at least one elongate rod tapers from said first end to said second end.*

*20. A variable pressure reducing device for reducing high pressure in steam and liquid sampling lines, said device comprising:*

*first and second elongate passageways;*

*first and second elongate rods extending along said first and second passageways, respectively, wherein each rod of said first and second elongate rods has a length and a first end and a second end such that at least said first rod is free of a step and therefore smoothly tapered along a length from a relatively wide diameter at said first end to a relatively narrow diameter at said second end; and*

*first and second separate annular gaps between each passageway of said first and second elongate passageways and said first and second elongate rods extending therealong, respectively, wherein each gap of said first and second separate annular gaps has a linear, unstepped outer boundary along said length of said first and second elongate rods, respectively, such that fluid pressure decreases along said first passageway from said relatively narrow diameter of said second end of said first rod to said relatively wide diameter of said first end of said first rod.*

*21. The device of claim 20 wherein a diameter of each gap of said first and second separate annular gaps changes along a length of each gap of said first and second separate annular gaps.*

* * * * *